United States Patent
Peterson et al.

(10) Patent No.: US 11,244,759 B2
(45) Date of Patent: *Feb. 8, 2022

(54) CONTEXTUALLY GROUPING SENSOR CHANNELS FOR HEALTHCARE MONITORING

(71) Applicant: Verily Life Sciences LLC, Mountain View, CA (US)

(72) Inventors: Bret Edward Peterson, Lafayette, CA (US); Dan Viet Duong, Los Altos Hills, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 156 days.

This patent is subject to a terminal disclaimer.

(21) Appl. No.: 16/700,395

(22) Filed: Dec. 2, 2019

(65) Prior Publication Data

US 2020/0105411 A1  Apr. 2, 2020

Related U.S. Application Data

(63) Continuation of application No. 15/829,399, filed on Dec. 1, 2017, now Pat. No. 10,497,475.

(51) Int. Cl.
*G16H 40/67* (2018.01)
*G16H 50/30* (2018.01)

(52) U.S. Cl.
CPC ............. *G16H 40/67* (2018.01); *G16H 50/30* (2018.01)

(58) Field of Classification Search
CPC ... A61B 5/681; A61B 5/4812; A61B 5/02427; A61B 5/02438; A61B 5/0002; A61B 5/002; A61B 5/0022; G06F 19/3418; G16H 50/20; G16H 50/30; G16H 40/67; G16H 10/60

See application file for complete search history.

(56) References Cited

U.S. PATENT DOCUMENTS

| | | |
|---|---|---|
| 7,411,196 B2 | 8/2008 | Kalayeh |
| 8,423,378 B1 | 4/2013 | Goldberg |
| 8,622,901 B2 | 1/2014 | Jain et al. |
| 8,872,664 B2 | 10/2014 | Bischoff et al. |
| 8,956,294 B2 | 2/2015 | McCombie et al. |
| 9,418,509 B2 | 8/2016 | Case, Jr. et al. |
| 9,672,731 B2 | 6/2017 | Vonder et al. |
| 9,694,239 B2 | 7/2017 | Case, Jr. et al. |
| 2008/0147438 A1 | 6/2008 | Kil |
| 2010/0250497 A1 | 9/2010 | Redlich et al. |
| 2013/0066815 A1 | 3/2013 | Oka et al. |

(Continued)

FOREIGN PATENT DOCUMENTS

WO  2012/061827 A2  5/2012

OTHER PUBLICATIONS

International Application No. PCT/US2018/062972, International Search Report & Written Opinion, 7 pages, dated Mar. 21, 2019.

(Continued)

*Primary Examiner* — Jonathan Durant

(57) ABSTRACT

The technology described herein is directed to a health-monitoring service that facilitates contextual grouping of sensor channels for healthcare monitoring. In some implementations, clustering algorithms and predictive models can be used to dynamically select the sensor channels associated with a mobile communication device that are monitored. In this manner, only those sensor channels that provide meaningful signals are monitored.

20 Claims, 9 Drawing Sheets

(56) References Cited

U.S. PATENT DOCUMENTS

| | | |
|---|---|---|
| 2014/0221789 A1 | 8/2014 | Pacione et al. |
| 2014/0303457 A1 | 10/2014 | Pipke |
| 2015/0160015 A1 | 6/2015 | DeWeese et al. |
| 2015/0170292 A1 | 6/2015 | Fung et al. |
| 2015/0282767 A1 | 10/2015 | Stivoric et al. |
| 2015/0317565 A1 | 11/2015 | Li et al. |
| 2016/0302671 A1 | 10/2016 | Shariff et al. |
| 2016/0317067 A1 | 11/2016 | Lee |
| 2017/0258390 A1 | 9/2017 | Howard |
| 2018/0074571 A1 | 3/2018 | Cronin et al. |

OTHER PUBLICATIONS

Qassem, Tarik et al., "Emerging Technologies For Monitoring Behavioural and Psychological Symptoms of Dementia," The 9th International Conference on P2P, Parallel, Grid, Cloud and Internet Computing, 9 pages, Nov. 2014.

Wood, Anthony D. et al., "Context-Aware Wireless Sensor Networks For Assisted Living and Residential Monitoring," IEEE Network, pp. 26-33, Jul./Aug. 2008.

Yefimova, Maria et al., "Using Sensor Technology to Monitor Disruptive Behavior of Persons With Dementia," AAAI Technical Report FS-12-01, pp. 51-54, 2012.

European Patent Application No. 18882428.8, Extended European Search Report, 11 pages, dated Jul. 23, 2021.

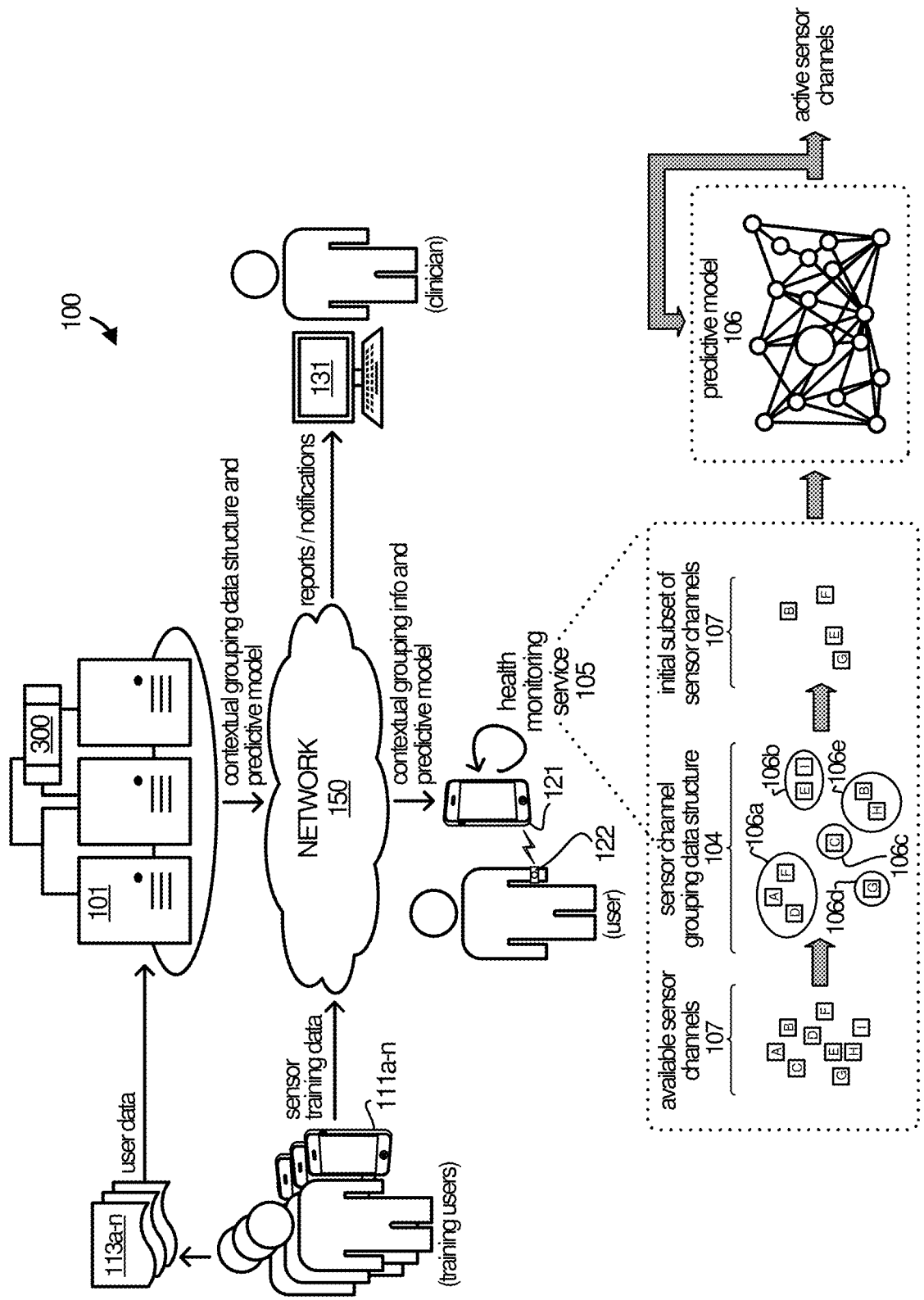

CONTEXTUALLY GROUPING SENSOR CHANNELS FOR HEALTHCARE MONITORING

CROSS-REFERENCE TO RELATED APPLICATIONS

This application is a continuation of and claims priority to U.S. patent application Ser. No. 15/829,399 titled "CONTEXTUALLY GROUPING SENSOR CHANNELS FOR HEALTHCARE MONITORING" filed on Dec. 1, 2017, which is expressly incorporated by reference herein.

BACKGROUND

Monitoring health-related conditions with optimal temporal resolution for at-risk patients or patients on new medications or treatments can be exceedingly difficult for clinicians. Some mobile health apps run on a mobile communication device associated with a patient (or user) to automatically monitor and promote multiple aspects of physical and emotional well-being by tracking patient behaviors along various health dimensions without requiring direct input from the patient.

Tracking a patient's behavior using these mobile health apps requires sampling each of multiple sensor channels and uploading the sensor data to a monitoring service. Because mobile communication devices often have numerous sensor channels capable of providing meaningful signals indicative of a patient's behavior, all or many of these signals must be sampled to accurately detect a health-related condition. Unfortunately, sampling these many sensor channels results in excessive power consumption which can result in non-compliance, uninstalling of a monitoring app, or device failure.

BRIEF DESCRIPTION OF THE DRAWINGS

In order to describe the manner in which the above-recited and other advantages and features can be obtained, a more particular description is set forth and will be rendered by reference to specific examples thereof which are illustrated in the appended drawings. Understanding that these drawings depict only typical examples and are not therefore to be considered to be limiting of its scope, implementations will be described and explained with additional specificity and detail through the use of the accompanying drawings.

FIGS. 1A-1C depict a block diagram illustrating an example operational environment including a health monitoring platform operable to contextually group sensor channels for healthcare monitoring, according to some implementations.

Figure 1A:
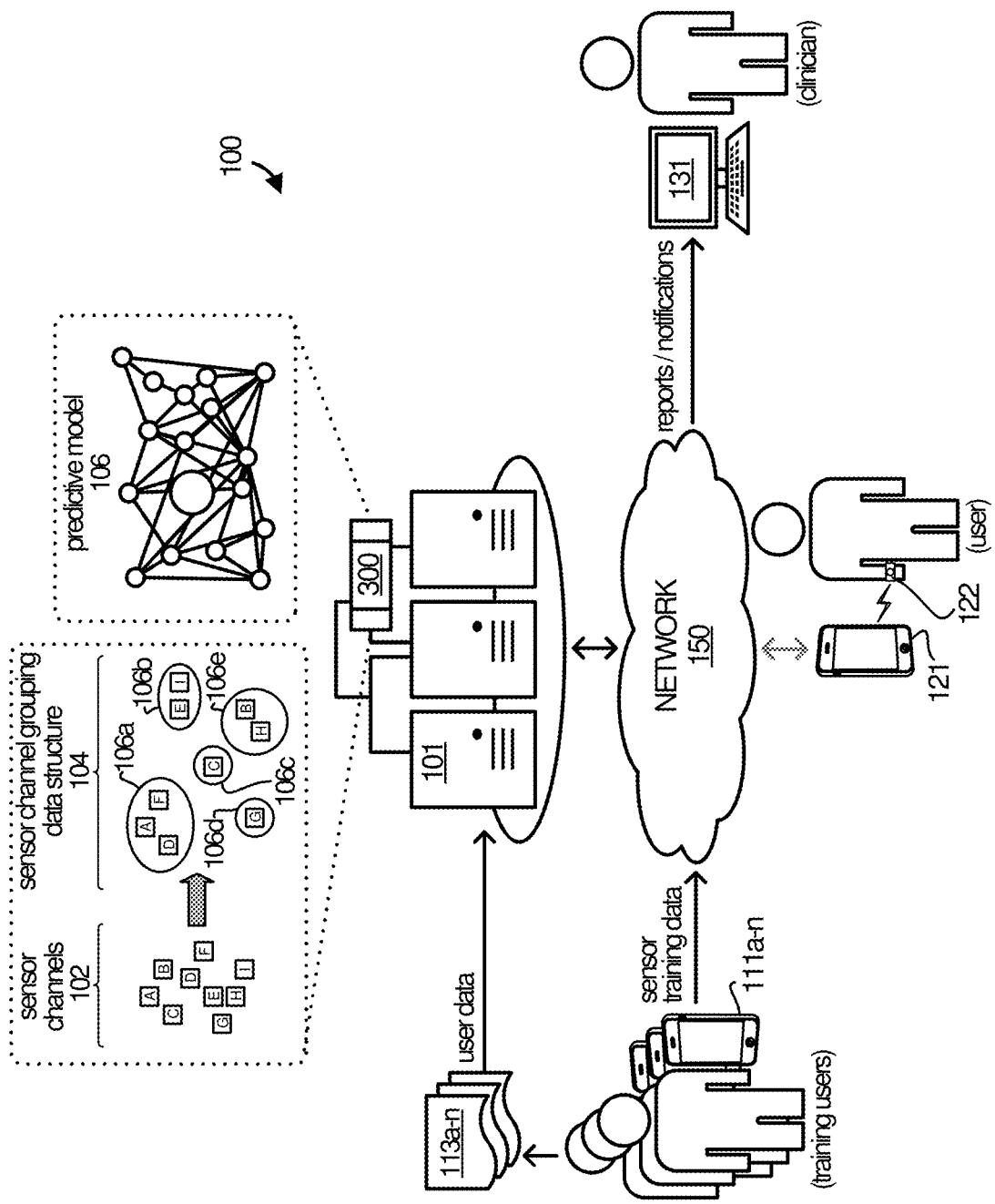

The drawings have not necessarily been drawn to scale. Similarly, some components and/or operations may be separated into different blocks or combined into a single block for the purposes of discussion of some of the embodiments of the present technology. Moreover, while the technology is amenable to various modifications and alternative forms, specific embodiments have been shown by way of example in the drawings and are described in detail below. The intention, however, is not to limit the technology to the particular embodiments described. On the contrary, the technology is intended to cover all modifications, equivalents, and alternatives falling within the scope of the technology as defined by the appended claims.

DETAILED DESCRIPTION

Examples are discussed in detail below. While specific implementations are discussed, it should be understood that this is done for illustration purposes only. A person skilled in the relevant art will recognize that other components and configurations may be used without parting from the spirit and scope of the subject matter of this disclosure. The implementations may include machine-implemented methods, computing devices, or computer readable medium.

There are many sensor channels associated with a mobile communication device that can provide meaningful signals indicative of a patient's well-being. However, as noted above, sampling each of these sensor channels is impractical as it can result in excessive power consumption leading to, among other things, noncompliance or uninstalling of health monitoring apps (or services).

The technology described herein is directed to a health-monitoring service that facilitates contextual grouping of sensor channels for healthcare monitoring. In some implementations, clustering algorithms and predictive models can be used to dynamically select (and re-select) the sensor channels associated with a mobile communication device that are monitored. In this manner, only sensor channels that provide meaningful signals are monitored.

The sensor channels can include traditional sensor outputs as well as non-traditional sensor outputs or indicators. For example, outputs or indicators from one or more software or hardware components, e.g., Bluetooth™ transmitters, Wi-Fi transmitters, cellular signal strength indicators, etc., can be sensor channels. Monitoring of the sensor channels can be continuous or non-continuous. Senor channels can be interrupt channels or polling channels. In some implementations, sensor channel outputs can be monitored substantially in real-time (or near real-time where a timestamp of the output is substantially immediate to actual time the output is received by a processing system). Outputs can alternatively or additionally be asynchronously retrieved or received.

At least one technical effect enabled by the techniques discussed herein is the ability for a mobile communication device to monitor sensor channels for accurate detection of a health-related condition while reducing power consumption of the mobile communication device. Advantageously, the reduction in power consumption results in increased compliance and decreased likelihood that a monitoring app (or service) is uninstalled.

Figure 1B:
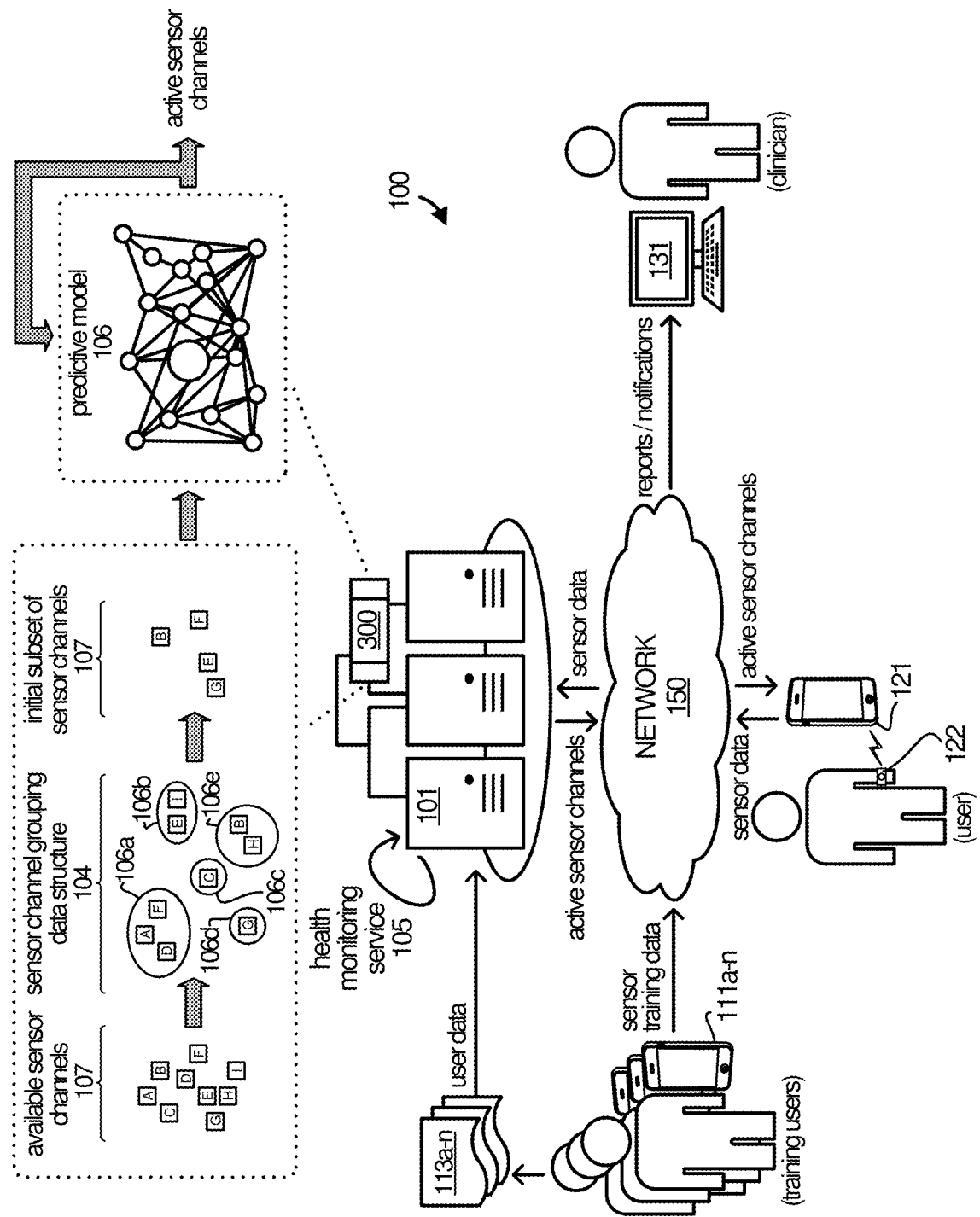

FIGS. 1A-1C depict a block diagram illustrating an example operational environment 100 including a health monitoring platform 101 operable to contextually group sensor channels for healthcare monitoring, according to some implementations. The example operational environment 100 includes health monitoring platform 101, various mobile communication devices 111*a-n* associated with training users, a mobile communication device 121 associated with a user (or patient), a communication device 131 associated with a clinician, and network 150. Additional or fewer systems or components are possible.

The health monitoring platform 101 is configured to generate a sensor channel grouping data structure 104 and at least one predictive model 106 associated with a predetermined health-related condition. In some implementations, the health monitoring platform 101 performs one or more health monitoring services 105 for detecting a predetermined health-related condition using the sensor channel grouping data structure 104 and the at least one predictive model 106. The sensor channel grouping data structure 104 identifies groups of sensor channels that provide overlapping data for detecting the predetermined health-related condition. As discussed herein, the health monitoring services can be performed in whole or in part by the health monitoring platform 101 (FIG. 1B) or a mobile communication device associated with a user, e.g., mobile communication device 121 (FIG. 1C). Accordingly, in some implementations, the sensor channel grouping data structure 104 and/or some or all components of a predictive model 106 can be pushed to a mobile communication device associated with a user (or patient), e.g., mobile communication device 121, for performing the health monitoring services.

Referring first to FIG. 1A, initially, the health monitoring platform 101 collects (or receives) training data from various training users and/or various mobile training communication devices 111*a-n* associated with the training users. The training data can include user data 113*a-n* and corresponding sensor training data. The user data can be any information that indicates that a user has (or does not have) a particular health-related condition. For example, if the health-related condition being monitored is depression, a user can self-report that he or she is depressed or has previously suffered from depression. The training data can alternatively or additionally include self- or clinician-administered examinations, e.g., questionnaires 113*a-n*, etc. For instance, user data can include a self-administered diagnostic instrument such as, for example, the Patient Health Questionnaire (PHQ-9), if the health-related condition being monitored is depression. The user data 113*a-n* can be provided directly to health monitoring platform 101, can be provided via mobile training communication devices 111*a-n*, or can be provided, in bulk or in whole, in another manner.

As discussed herein, the health monitoring platform 101 also collects (or receives) corresponding sensor training data from the various communication devices 111*a-n* associated with the training users. The sensor training data can include sensor data sampled by various sensor channels associated with each of the communication devices 111*a-n*.

The health monitoring platform 101 processes the user data to identify training users that have the predetermined health-related condition. The health monitoring platform 101 then correlates the sensor training data received from the training users that are identified as having the predetermined health-related condition to identify the sensor channels 102 that provide information relevant for detecting the predetermined health-related condition. The health monitoring platform 101 then correlates the sensor channels 102 that provide the information relevant for detecting the predetermined health-related condition to identify the sensor channels that provide overlapping sensor data. In some implementations, a sensor channel grouping data structure 104 is generated that identifies contextual groups of sensor channels that provide overlapping outputs. That is, the sensor channels that provide overlapping sensor data can be clustered into multiple sensor groups associated with a particular predetermined health-related condition or multiple pre-determined conditions. As discussed herein, the overlapping data can be any sensor data that is interchangeable for the purpose of detecting one or more health-related condition. For example, location information can be provided by a Global Positioning System (GPS) sensor or one or more other sensor channels, e.g., Wi-Fi sensors, etc.

In some implementations, sensor channel grouping data structure 105 can be a sensor matching table or other grouping model that identifies the overlapping sensor data. The sensor channel grouping data structure can be layered or hierarchically formatted or arranged. For example, in some implementations, each layer of the sensor channel grouping data structure 104 can be associated with overlapping sensor data clustered into multiple sensor groups associated with a particular predetermined health-related condition.

In some implementations, the health monitoring platform 101 can correlate the sensor channels prior to making a determination about which sensor channels provide information relevant for detecting one or more the predetermined health-related condition. For example, the health monitoring platform 101 can correlate all or part of the sensor training data to identify the sensor channels that provide overlapping sensor data. However, in some instances, the predetermined health-related condition can be relevant in determining whether the sensor channels provide overlapping sensor data. For example, two sensor channels can be correlated although they provide different sensor data if the sensor data that the sensor channels provide is interchangeable, e.g., sensor data from either channel can be used to infer a particular state or condition.

Regardless, once the health monitoring platform 101 identifies the sensor channels 102 that provide the overlapping sensor data, the health monitoring platform 101 generates sensor channel grouping data structure 104 by clustering the sensor channels that provide the overlapping sensor data into multiple contextual sensor groups 106*a*-106*e*. As discussed herein, the sensor channel grouping data structure can be used by a health monitoring service 105 to facilitate dynamic selection of active sensor channels for monitoring (see FIGS. 1B and 1C).

The health monitoring platform 101 also processes the user data and corresponding sensor training data to generate one or more predictive models, e.g., predictive model 106. In some implementations, predictive model 106 operates on the health monitoring platform 101 to infer a health-state of the user based on the outputs of an active group of sensor channels being monitored by a mobile communication device, e.g., mobile communication device 121, in order to predict, based on the outputs of the active group of sensor channels, whether particular sensor channels should be deactivated or whether other sensor channels should be activated. For example, predictive model 106 can infer a state of a user based on outputs of the active group of sensor channels and predict, based on the inferred state of the user, the sensor channels that are likely to provide meaningful signals during an upcoming period of time. These sensor channels can be activated or added to the group of sensor channels that are being monitored. Likewise, predictive model 106 can predict, based on the inferred state of the user, that one or more of the active sensor channels currently being monitored is not likely to provide meaningful signals during the upcoming period of time. In this manner, the health monitoring service 105 monitors only those sensor channels that are likely to provide meaningful signals which reduces the power consumption (or usage) of the mobile communication device.

In some implementations, the predictive model 106 is pushed out to a mobile communication device, e.g., mobile communication device 121, for local use or execution by the mobile communication device.

In some implementations, the predictive model 106 can include one or more classification engines (or algorithms) which operate to infer a patient's health state, e.g., estimated sleep duration, physical activity level, social interaction, etc. Each classification engine can use, among other data, one or more sensor channel outputs to make the inferences. Additional or fewer classification engines are possible. Example classification engines are shown and discussed in greater detail with reference to FIG. 2.

Once the sensor channel grouping data structure and predictive model is generated, a health monitoring service 105 can monitor the health state of an individual user in order to monitor for and/or detect a health-related condition. The health monitoring service 105 can be performed (or executed) at or on the health monitoring platform 101 (FIG. 1B) or locally at or on the mobile communication device 121 associated with the user (FIG. 1C).

In operation, the health monitoring service 105 first identifies sensor channels associated with mobile communication device 121 that are available for monitoring, e.g., available sensor channels 107. As discussed herein, the available sensor channels 107 can include sensor channels that are physically available (or present) as well as virtual sensor channels that are derived based on some physical sensor(s) or indicator(s). Additionally, the available sensor channels 107 are accessible to the monitoring service (or app) 105. That is, the monitoring service (or app) 105 should have permission to access each of the available sensor channels 107. In some implementations, permission is received at the time of installation of the monitoring app (or service) 105.

The available sensor channels 107 can include both internal sensor channels and external sensor channels that provide output information to mobile communication device 121, e.g., watches and other peripheral devices in communication with the mobile communication device via a Bluetooth™ connection or other wireless or non-wireless connection. For example, an external sensor channel can be a smart watch 122 that includes one or more sensor channels that collect and provide the data to the corresponding mobile communication device 121.

As noted above, the sensor channels can include traditional sensor outputs as well as non-traditional sensor outputs or indicators. For example, outputs or indicators from one or more software or hardware components, e.g., Bluetooth™ transmitters, Wi-Fi transmitters, cellular signal strength indicators, etc., can be sensor channels. Monitoring of the sensor channels can be continuous or non-continuous. Senor channels can be interrupt channels or polling channels. In some implementations, sensor channel outputs can be monitored substantially in real-time (or near real-time where a timestamp of the output is substantially immediate to actual time the output is received by a processing system). Outputs can alternatively or additionally be asynchronously retrieved or received.

The health monitoring service 105 then selects an initial subset (or group) of sensor channels 107 from the available sensor channels 107 based on the sensor grouping data structure 104. The sensor grouping data structure 104 is configured to identify contextual groups of sensor channels that provide overlapping outputs. As discussed herein, the overlapping outputs are outputs that are interchangeable for the purpose of detecting one or more predetermined health-related conditions. Once selected, the health monitoring service 105 activates the sensor channels for monitoring. As shown in the example of FIG. 1B, a message or indication identifying the active sensor channels is sent by the health monitoring platform 101 for delivery to the mobile communication device 121 when the health monitoring service 105 is running or executing on the health monitoring platform 101.

The outputs of the active sensor channels are monitored and fed to the predictive model 106 which, in turn, uses the outputs to infer a health-state of a user associated with mobile communication device 121 based on the outputs. The health monitoring service 105 dynamically re-selects the active sensor channels in an iterative or recursive manner based on the health-state of the user. As discussed herein, the re-selection can include deactivating, activating, or both, from the available sensor channels 107 such that the health monitoring service 105 monitors only those sensor channels that are likely to provide meaningful signals and, thus, reduces the power consumption (or usage) of the mobile communication device.

The health monitoring platform 101 is representative of any cloud service or collection of services that is configured to facilitate adaptive contextual grouping of sensor channels for healthcare monitoring. The health monitoring platform 101 may include server computers, blade servers, rack servers, and any other type of computing system (or collection thereof) suitable for executing the monitoring service and/or otherwise carrying out the operations discussed herein. Such systems may employ one or more virtual machines, containers, or any other type of virtual computing resource in the context of monitoring a particular or predetermined health-related condition or generating and pushing out a monitoring service of which computing system 601 of FIG. 6 is representative.

Figure 6:
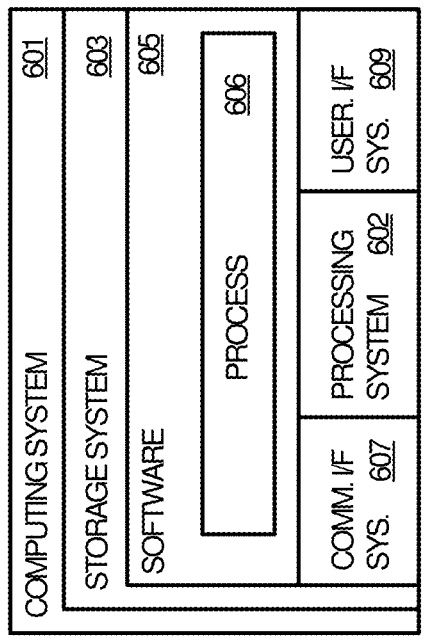
FIG. 6 depicts a block diagram illustrating an example computing system suitable for implementing the technology disclosed herein, including any of the applications, architectures, elements, processes, and operational scenarios and sequences illustrated in the Figures and discussed below in the Technical Disclosure.

Mobile communication devices 111*a-n* and 121 are representative of any mobile computing device, such as a desktop computer, laptop, tablet, or mobile phone, of which computing system 601 of FIG. 6 is representative.

Figure 2:
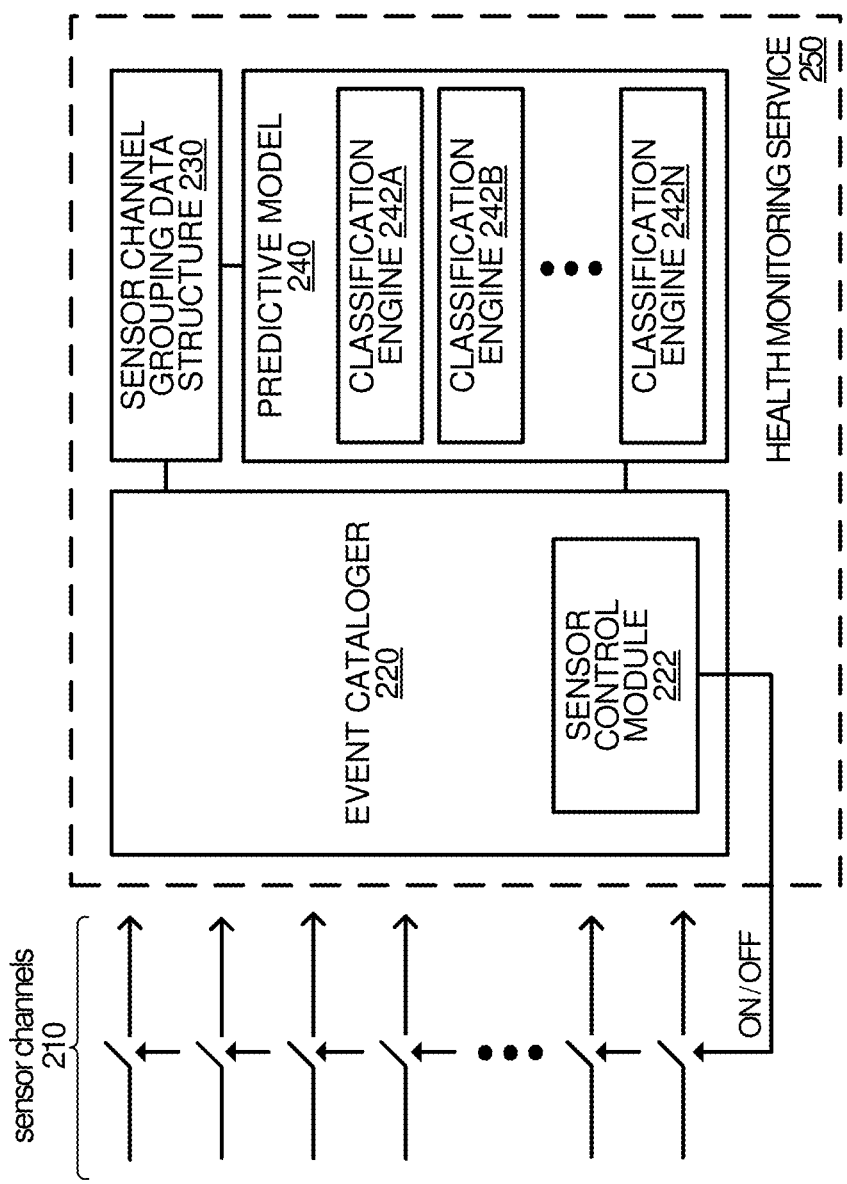
FIG. 2 depicts example components of a health monitoring service, according to some implementations.

FIG. 2 depicts example components of a health monitoring service 200, according to some implementations. The health monitoring service 200 can be health monitoring service 105 of FIG. 1B or FIG. 1C, although alternative configurations are possible. As discussed herein, the components of the monitoring service 200 can be executed on mobile communication device such as, for example, mobile communication device 121 of FIG. 1, or on a health monitoring platform such as, for example, health monitoring platform 101 of FIG. 1. In some implementations, the components of the monitoring service 200 can be distributed across a mobile communication device and a health monitoring platform.

As illustrated in the example of FIG. 2, the monitoring service 200 includes an event cataloger 220, sensor channel grouping data structure 230 and a predictive model 240. Other components are also possible.

Event cataloger 220 is communicatively coupled with sensor channels 210 and is configured to control which sensor channels 210 are ON/OFF (e.g., enabled/disabled). At any given time, the enabled (or activated) sensor channels are part of the active group of sensor channels that are being monitored. The event cataloger 220 includes a sensor control module 222 that controls whether the sensor channels are ON/OFF.

The sensor channel grouping data structure 230 is configured to identify groups of sensor channels that provide overlapping data for detecting one or more health-related conditions. In some implementations, the sensor channel grouping data structure 230 can also include preferred sensor channels or other information. For example, assuming multiple sensor channels in a group are available for monitoring, default sensor information may be included and/or predicted power consumption information.

Predictive model 240 is configured to infer a state of the user based on the outputs of an active group of sensor channels 210 being monitored in order to predict the sensor channels that are likely to provide meaningful signals. As shown in the example of FIG. 2, the predictive model 240 includes classification engines (or algorithms) 142a-142n. The classification engines (or algorithms) 142a-142n operate to infer a user's state, e.g., estimated sleep duration, physical activity level, social interaction, etc.

In some implementations, each classification engine 142a-142n can use, among other data, one or more sensor channels to make the inferences. For example, one or more of various sensor channel outputs can be used to infer physical activity, sleep or a sleep-like state, or various other health-related states. For example, ambient light sensors, microphones, etc., can be used in combination to infer an unconscious state.

In some implementations, the predictive model 240 is also adapted to identify personalization's. For example, if a particular feature or sensor channel is never used by a user (or patient), then the sensor channel can be turned off automatically by the health monitoring service, e.g., SmsTextMessagesSensor can be turned off if the user uses a data plan to send text messages rather than SMS. Likewise, sensor channels can be used to determine whether other sensor channels are ON or OFF. For example, sensor channels that provide location information can be shut OFF when the user is at home sleeping because the user's location will not change while sleeping.

In some implementations, the health monitoring service can implement adaptive sampling (or throttling) of one or more sensor channels. For example, if rates of change of a sensor channel output are low for an extend period, then the rate at which the service samples the sensor channel can be reduced toward a minimum sampling rate. Likewise, if the rate of change increases, then the rate at which the service samples the sensor channel can be increase toward a maximum sampling rate. Additionally, as noted above, the sampling rates can be adjusted depending on battery level or other mobile device specific information.

In some implementations, sensitivity analysis can be applied to the health-states to determine relative contribution of different sensor channels to classifying a derived health-state. In such instances, less critical sensor channels are more likely to be turned off relative to other sensor channels with the same impact on battery life. In some implementations, a machine learning model is used to optimize which sensor channels are turned on at any given time based on rated derived feature production (by classifier models) or estimated sensor output information content, and battery life.

Figure 3:
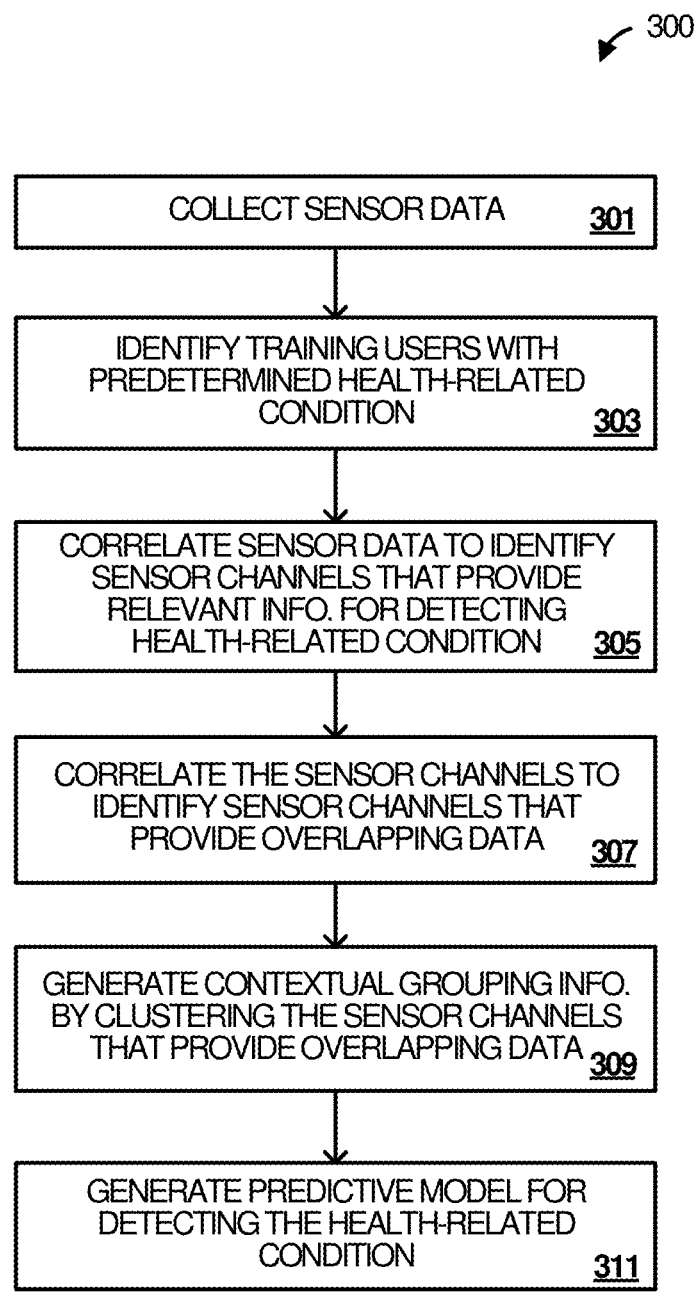
FIG. 3 depicts a flow diagram illustrating example operations for generating a predictive model and a sensor channel grouping data structure for healthcare monitoring, according to some implementations.

FIG. 3 depicts a flow diagram illustrating example operations 300 for generating a predictive model and a sensor channel grouping data structure for healthcare monitoring, according to some implementations. The example operations 300 may be performed in various implementations by a healthcare monitoring platform such as, for example, healthcare monitoring platform 101 of FIG. 1, or one or more microcontrollers, modules, engines, or components associated therewith.

To begin, at 301, the healthcare monitoring platform collects sensor data from multiple sensor channels on multiple mobile communication devices associated with multiple training users. Alternatively, the sensor data can be provided to the healthcare monitoring platform in bulk. At 303, the healthcare monitoring platform processes the sensor data to identify the training users that have a predetermined health-related condition.

At 305, the healthcare monitoring platform correlates the sensor data associated with the training users having the health-related condition to identify sensor channels that provide information that is relevant for detecting the health-related condition. At 307, the healthcare monitoring platform correlates the sensor channels that provide the information that is relevant for detecting the health-related condition to identify the sensor channels that provide overlapping sensor data.

At 309, the healthcare monitoring platform generates sensor channel grouping data structure by clustering the sensor channels that provide the overlapping sensor data into multiple contextual sensor groups. Lastly, at 311, the healthcare monitoring platform generates a predictive model for detecting the health-related condition based on the sensor data collected from the sensor channels that provide the information that is relevant for detecting the health-related condition.

Figure 4:
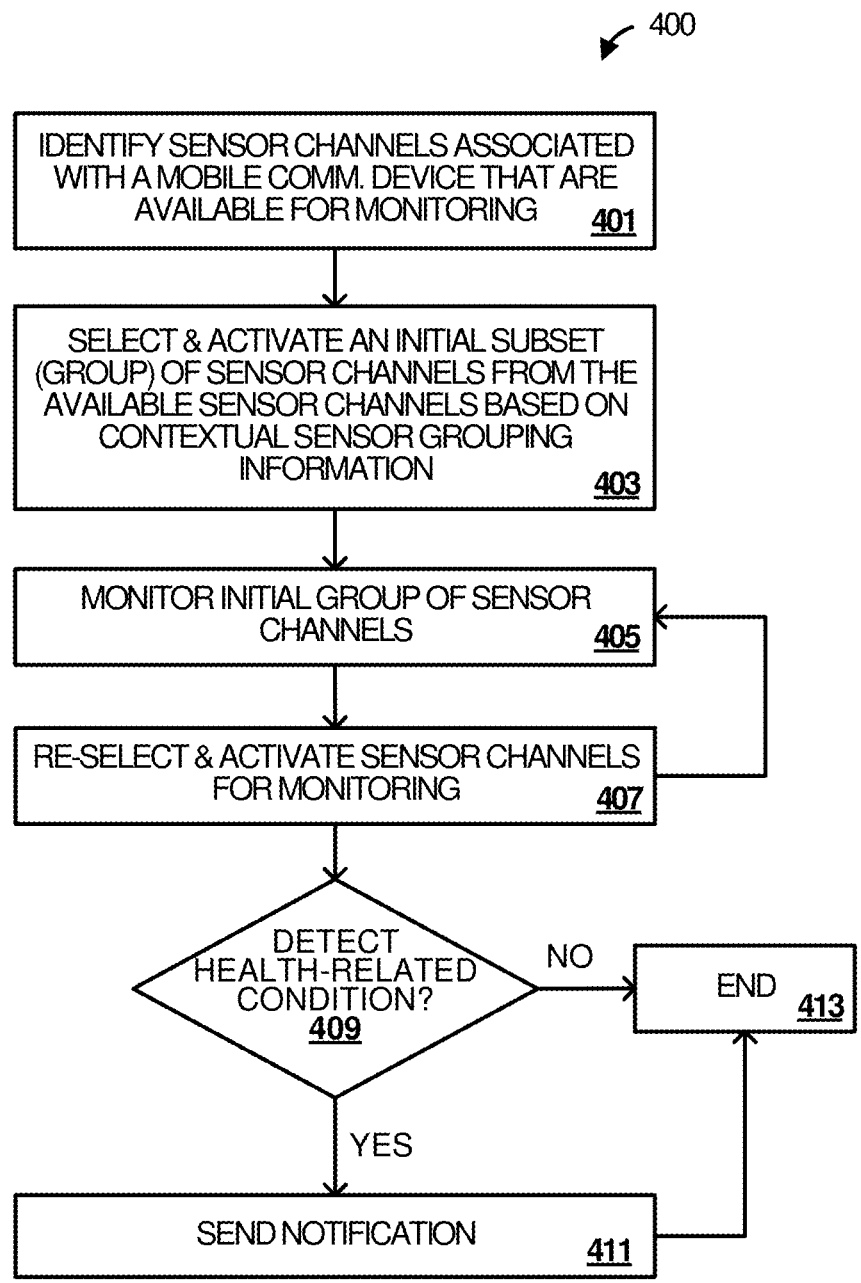
FIG. 4 depicts a flow diagram illustrating example operations of a health monitoring service for detecting a health-related condition by monitoring an active group of sensor channels while dynamically re-selecting the group of active sensor channels, according to some implementations.

FIG. 4 depicts a flow diagram illustrating example operations 400 of a health monitoring service for detecting a health-related condition by monitoring an active group of sensor channels while dynamically re-selecting the group of active sensor channels, according to some implementations. The example operations 400 may be performed in various implementations by a health monitoring service such as, for example, health monitoring service 105 of FIG. 1, or one or more microcontrollers, modules, engines, or components associated therewith.

As discussed herein, the health monitoring service can be performed (or executed) at or on a health monitoring platform, e.g., health monitoring platform 101 of FIG. 1B, or at or on a mobile communication device associated with the user, e.g., mobile communication device 121 of FIG. 1C. To begin, at 401, the health monitoring service identifies sensor channels associated with a mobile communication device corresponding to a user (or patient) that are available for monitoring. As discussed herein, the available sensor channels can include both internal sensor channels and external sensor channels that provide sensor information to the particular mobile communication device, e.g., watches and other peripheral devices in communication with the mobile communication device via a Bluetooth™ connection. Additionally, the sensor channels can include both traditional sensor outputs as well as non-traditional sensor outputs or indicators.

At 403, the health monitoring service selects an initial subset (or group) of sensor channels from the sensor channels associated with the mobile communication device that are available for monitoring based on a sensor channel grouping data structure. The sensor channel grouping data structure identifies multiple groups of sensor channels that provide overlapping data for detecting one or more predetermined health-related conditions. More specifically, the overlapping outputs can be outputs that are interchangeable for the purpose of detecting one or more predetermined health-related conditions. In some implementations, the initial subset includes sensor channels are selected such that the channel outputs do not overlap or that have minimal overlap.

At 405 and 407, the health monitoring service monitors active sensor channels starting with the initial subset of sensor channels while dynamically re-selecting the active sensor channels in an iterative or recursive manner based on outputs of the predictive model while maintaining little or no overlap in the active sensor channel outputs. Although not shown, in some implementations, the health monitoring service also dynamically adjusts a sampling rate of one or more of the active sensor channels in an iterative or recursive manner based on one or more of the health-state of the user and/or status information associated with the mobile communication device. For example, if an activity recognition sensor channel is sufficient, then the health monitoring service might not separately sample an accelerometer at very high sampling rates to determine if a user (patient) is walking. However, the health monitoring service might still sample the accelerometer at a much lower rate for other purposes or classifications, e.g., if it is important to determine whether the user is carrying their phone.

As discussed herein, the outputs of the active sensor channels are fed (or provided) to the predictive model. The predictive model infers a health-state of a user associated with the mobile communication device using the outputs. The active sensor channels can then be dynamically adjusted based on the health-state of the user. The predictive model can determine, based on the inferred state of the user, the sensor channels that are currently likely to provide meaningful signals. For example, if a user is sleeping, particular sensor channels may not be useful and, therefore, turned OFF or deactivated. Likewise, other sensor channels may be deemed useful and, therefore, turned ON or activated. Alternatively, rather than turning sensor channels completely ON or OFF, sample or polling rates can be increased or reduced as necessary.

In some implementations, responsive to a change in the health-state of the user, the health monitoring service can identify, from the active sensor channels, sensor channels having outputs with decreased relevance for detecting a predetermined health-related condition and deactivate those sensor channels. Likewise, responsive to a change in the health-state of the user, the health monitoring service can identify, from the available sensor channels, sensor channels having outputs with increased relevance for detecting the predetermined health-related condition and activate those sensor channels. Additionally, the sensor channels can be dynamically re-selected based on status information associated with the mobile communication device. For example, status information can be information relating to power consumption of one or more sensor channels or battery status information associated with the mobile communication device.

At decision 409, the mobile communication device determines if the health-related condition is detected. If so, at 411, the mobile communication device sends a notification indicating occurrence of the health-related condition. Otherwise, at 411, the mobile communication device ends the query.

Figure 5A:
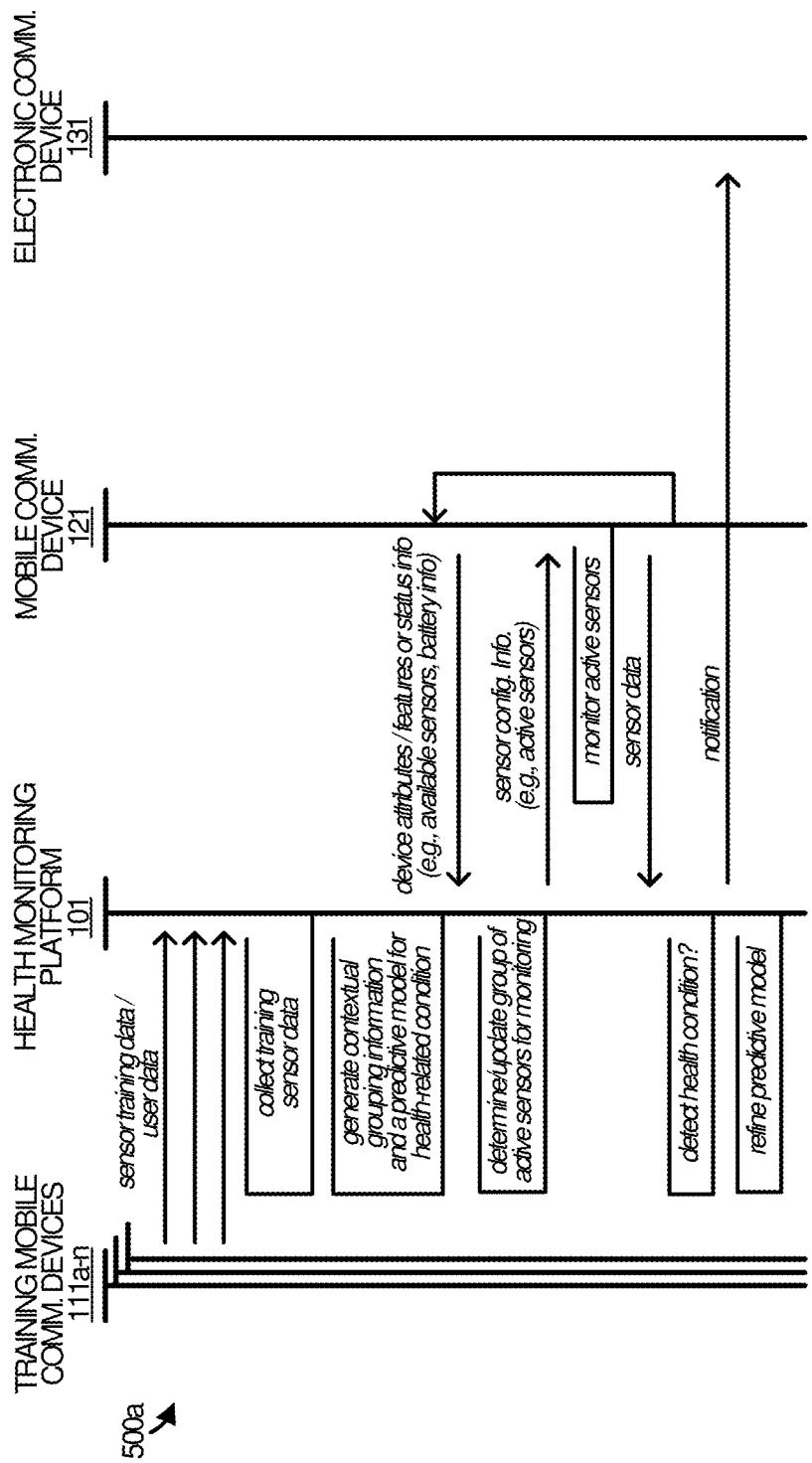
FIGS. 5A and 5B depict sequence diagrams illustrating example operations of components of the operational environment, according to some implementations.
Figure 5B:
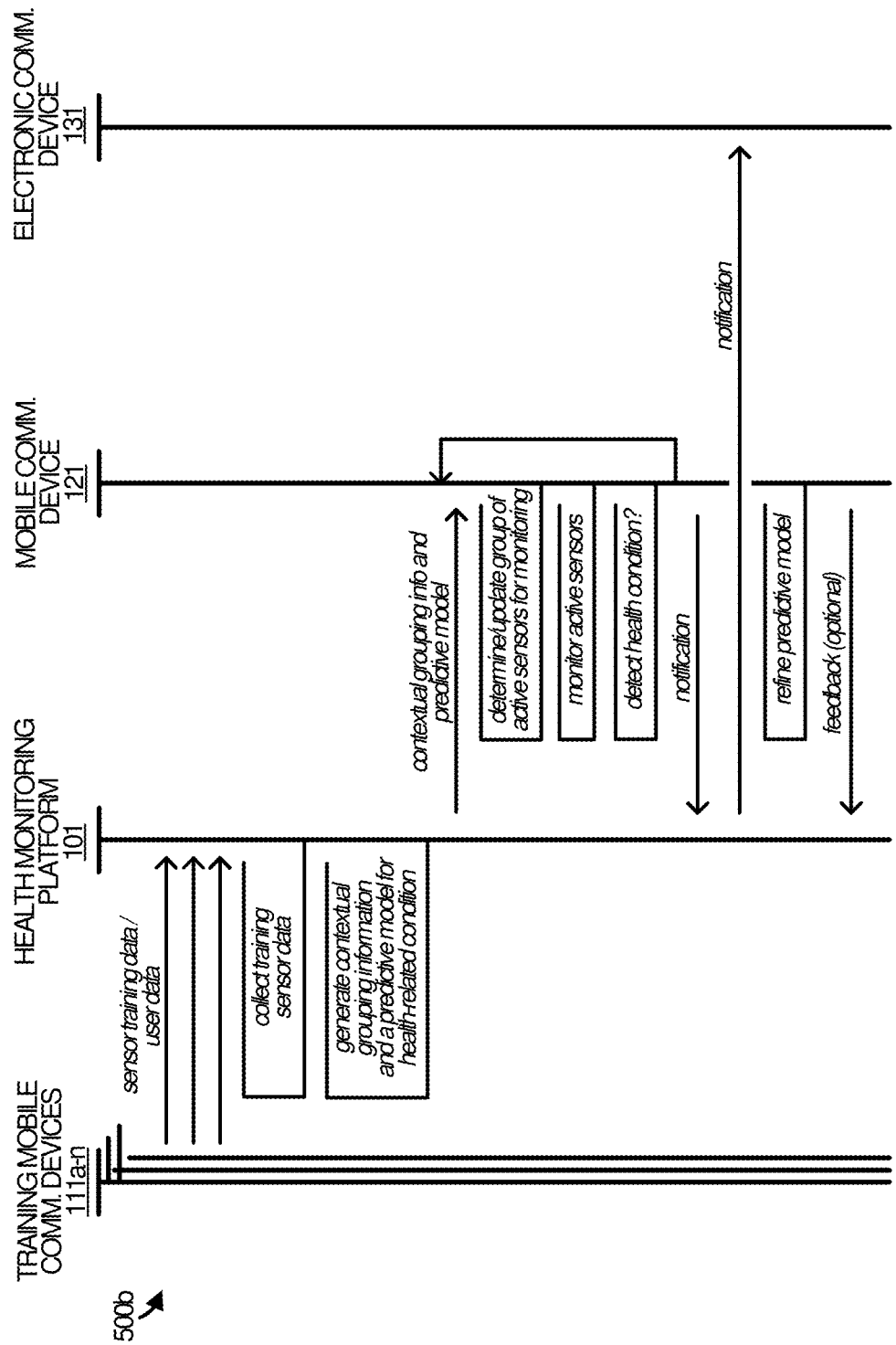

FIGS. 5A and 5B depict sequence diagrams 500a and 500b illustrating example operations of components of the operational environment 100, according to some implementations. As shown in the example of FIGS. 5A and 5B, the sequence diagrams 500a and 500b include health monitoring platform 101, various mobile communication devices 111a-n, a mobile communication device 121 associated with a user, and a communication device 131 (or communication interface) associated with a clinician. Additional or fewer components are possible.

Referring first to FIG. 5A, to begin, the training mobile communication devices 111a-n send user data and corresponding sensor training data and to the health monitoring service platform 101. The health monitoring platform 101 collects and/or otherwise receives the user data and the corresponding sensor training data. As discussed above, the user data can be any information that indicates that a user has a particular health-related condition. Likewise, the sensor training data can include sensor data sampled by available sensor channels from each of the multiple mobile communication training communication devices 111a-n associated with the training users. As discussed herein, the available sensor channels for a particular mobile communication device can include both internal sensor channels and externals sensor channels that provide sensor information to the particular mobile communication device.

Once the data is collected, the health monitoring platform 101 processes the user data to identify the training users that have the predetermined health-related condition and then correlates the sensor training data received from the training users that are identified as having the predetermined health-related condition to identify the sensor channels that provide information relevant for detecting the predetermined health-related condition. The health monitoring platform 101 correlates the sensor channels that provide the information relevant for detecting the predetermined health-related condition to identify the sensor channels that provide overlapping sensor data. As discussed herein, a first sensor channel can provide overlapping data with a second sensor channel if the sensor data provided by the first channel is interchangeable with the sensor data provided by the second channel for the purpose of detecting a particular health-related condition.

Once the health monitoring platform 101 identifies the sensor channels that provide the overlapping sensor data, the health monitoring platform 101 generates a sensor channel grouping data structure by clustering the sensor channels that provide the overlapping sensor data into multiple contextual sensor groups. As discussed herein, the sensor channel grouping data structure (along with one or more predicative models) can be used to facilitate dynamic selection of active sensor channels for monitoring by a mobile communication device associated with a user, e.g., mobile communication device 121.

The health monitoring platform 101 also processes the user data to generate a predictive model associated with a particular health-related condition. In some implementations, the predictive model operates on the health monitoring platform 101 to infer a state of the user based on the outputs of an active group of sensor channels being monitored by a mobile communication device 121, e.g., mobile communication device 121, in order to predict whether particular sensor channels should be deactivated or whether other sensor channels should be activated.

The health monitoring platform 101 receives device attributes (or features) and/or status information from the mobile communication device 121. The device attributes (or features) and/or status information can include, for example, sensor channels that are available for monitoring by a service running on the mobile communication device 121. The sensor channels that are available for monitoring can be determined by the mobile communication device 121 based on the actual physical sensors on or in communication with mobile communication device 121, the sensor channels that are enabled, e.g., some sensor channels can be manually turned OFF, and the sensor channels for which the monitoring service has permission to access. That is, the monitoring service or app running on the mobile communication device 121 may have limited or no access to monitor some sensor channels. Device status information, e.g., battery information can also be sent to the health monitoring platform 101. For example, if the mobile communication device 121 is in a low battery state, fewer sensor channels may be selected for active monitoring. Likewise, if particular sensor channels are consuming a lot of energy, the information can be used by the health monitoring platform 101 to select a sensor channel that consumes less energy (from a group of overlapping sensor channels).

The health monitoring platform 101 then selects an active group of sensor channels from the sensor channels associated with the mobile communication device that are available for monitoring based on the sensor channel grouping data structure and the predictive model. As discussed above, the sensor channel grouping data structure identifies multiple groups of sensor channels that provide overlapping data for detecting a health-related condition. The health monitoring platform 101 then sends sensor configuration information identifying the active group of sensor channels to the mobile communication device 121.

The mobile communication device 121 monitors the active sensor channels and provides sensor data back to the health monitoring platform 101. In some implementations, the sensor data can be raw data sampled from the sensor channels. Alternatively, the sensor data can be anonymized for privacy reasons. For example, the sensor data can be hashed and associated with a phone number but not a name of the user. For example, text messages can be monitored, hashed, and transmitted to the health monitoring platform 101.

The health monitoring platform 101 processes the sensor data received from the mobile communication device 121 and determines if a health-related condition is detected. If so, a notification can be sent to a communication device 131 (or communication interface or portal) associated with a clinician. Lastly, the health monitoring platform 101 can refine the predictive model based on the outputs of the active sensor channels.

The example of FIG. 5B is similar to the example of FIG. 5A except that the health monitoring platform 101 sends (or pushes out) the sensor channel grouping data structure and the predictive model to mobile communication devices associated with users of the monitoring service. As shown in the example of FIG. 1C, the health monitoring platform 101 pushes the sensor channel grouping data structure and the predictive model to mobile communication device 121.

The mobile communication device 121 can identify device attributes (or features) and/or status information associated with the mobile communication device 121 as well as sensor channels that are available for monitoring. As noted above, the sensor channels that are available for monitoring can be determined by the mobile communication device 121 based on the actual sensors on or in communication with mobile communication device 121, the sensor channels that are enabled, e.g., some sensor channels can be manually turned OFF, and the sensor channels for which the monitoring service has permission to access.

The mobile communication device 121 then selects an active group of sensor channels from the sensor channels associated with the mobile communication device that are available for monitoring based on the sensor channel grouping data structure and the predictive model. As discussed above, the sensor channel grouping data structure identifies multiple groups of sensor channels that provide overlapping data for detecting a health-related condition.

The mobile communication device 121 processes the sampled sensor data from the mobile communication device 121 and determines if a health-related condition is detected. If so, a notification can be sent to a communication device (or communication interface) associated with a clinician.

Lastly, the mobile communication device 121 can optionally refine the predictive model based on the outputs of the active sensor channels and provide feedback to the health monitoring platform 101.

FIG. 6 illustrates computing system 601, which is representative of any system or collection of systems in which the various applications, services, scenarios, and processes disclosed herein may be implemented. For example, computing system 601 may include server computers, blade servers, rack servers, and any other type of computing system (or collection thereof) suitable for carrying out the enhanced collaboration operations described herein. Such systems may employ one or more virtual machines, containers, or any other type of virtual computing resource in the context of contextually grouping sensor channels for healthcare monitoring.

Computing system 601 may be implemented as a single apparatus, system, or device or may be implemented in a distributed manner as multiple apparatuses, systems, or devices. Computing system 601 includes, but is not limited to, processing system 602, storage system 603, software 605, communication interface system 607, and user interface system 609. Processing system 602 is operatively coupled with storage system 603, communication interface system 607, and an optional user interface system 609.

Processing system 602 loads and executes software 605 from storage system 603. When executed by processing system 602 for deployment of scope-based certificates in multi-tenant remote content and collaboration environments, software 605 directs processing system 602 to operate as described herein for at least the various processes, operational scenarios, and sequences discussed in the foregoing implementations. Computing system 601 may optionally include additional devices, features, or functionality not discussed for purposes of brevity.

Referring still to FIG. 6, processing system 602 may comprise a micro-processor and other circuitry that retrieves and executes software 605 from storage system 603. Processing system 602 may be implemented within a single processing device, but may also be distributed across multiple processing devices or sub-systems that cooperate in executing program instructions. Examples of processing system 602 include general purpose central processing units, application specific processors, and logic devices, as well as any other type of processing device, combinations, or variations thereof.

Storage system 603 may comprise any computer readable storage media readable by processing system 602 and capable of storing the software 605. Storage system 603 may include volatile and nonvolatile, removable and non-removable media implemented in any method or technology for storage of information, such as computer readable instructions, data structures, program modules, or other data. Examples of storage media include random access memory, read only memory, magnetic disks, optical disks, flash memory, virtual memory and non-virtual memory, magnetic cassettes, magnetic tape, magnetic disk storage or other magnetic storage devices, or any other suitable storage media. In no case is the computer readable storage media a propagated signal.

In addition to computer readable storage media, in some implementations the storage system 603 may also include computer readable communication media over which at least some of software 605 may be communicated internally or externally. Storage system 603 may be implemented as a single storage device, but may also be implemented across multiple storage devices or sub-systems co-located or distributed relative to each other. Storage system 603 may comprise additional elements, such as a controller, capable of communicating with processing system 602 or possibly other systems.

Software 605 may be implemented in program instructions and among other functions may, when executed by processing system 602, direct the processing system 602 to operate as described with respect to the various operational scenarios, sequences, and processes illustrated herein. For example, software 605 may include program instructions for directing the system to perform the processes described with reference to the Figures described herein.

In particular, the program instructions may include various components or modules that cooperate or otherwise interact to carry out the various processes and operational scenarios described herein. The various components or modules may be embodied in compiled or interpreted instructions, or in some other variation or combination of instructions. The various components or modules may be executed in a synchronous or asynchronous manner, serially or in parallel, in a single threaded environment or multi-threaded, or in accordance with any other suitable execution paradigm, variation, or combination thereof. Software 605 may include additional processes, programs, or components, such as operating system software, virtual machine software, or application software. Software 605 may also comprise firmware or some other form of machine-readable processing instructions executable by processing system 602.

In general, software 605 may, when loaded into processing system 602 and executed, transform a suitable apparatus, system, or device (of which the computing system 601 is representative) overall from a general-purpose computing system into a special-purpose computing system. Indeed, encoding software on storage system 603 may transform the physical structure of storage system 603. The specific transformation of the physical structure may depend on various factors in different implementations of this description. Examples of such factors may include, but are not limited to, the technology used to implement the storage media of storage system 603 and whether the computer-storage media are characterized as primary or secondary storage, as well as other factors.

For example, if the computer readable storage media are implemented as semiconductor-based memory, software 605 may transform the physical state of the semiconductor memory when the program instructions are encoded therein, such as by transforming the state of transistors, capacitors, or other discrete circuit elements constituting the semiconductor memory. A similar transformation may occur with respect to magnetic or optical media. Other transformations of physical media are possible without departing from the scope of the present description, with the foregoing examples provided only to facilitate the present discussion.

Communication interface system 607 may include communication connections and devices that allow for communication with other computing systems (not shown) over communication networks (not shown). Examples of connections and devices that together allow for inter-system communication may include network interface cards, antennas, power amplifiers, RF circuitry, transceivers, and other communication circuitry. The connections and devices may communicate over communication media to exchange communications with other computing systems or networks of systems, such as metal, glass, air, or any other suitable communication media. The aforementioned media, connections, and devices are well known and need not be discussed at length here.

User interface system 609 may include a keyboard, a mouse, a voice input device, a touch input device for receiving a touch gesture from a user, a motion input device for detecting non-touch gestures and other motions by a user, and other comparable input devices and associated processing elements capable of receiving user input from a user. Output devices such as a display, speakers, haptic devices, and other types of output devices may also be included in user interface system 609. In some cases, the input and output devices may be combined in a single device, such as a display capable of displaying images and receiving touch gestures. The aforementioned user input and output devices are well known in the art and need not be discussed at length here. In some cases, the user interface system 609 may be omitted when the computing system 601 is implemented as one or more server computers such as, for example, blade servers, rack servers, or any other type of computing server system (or collection thereof).

User interface system 609 may also include associated user interface software executable by processing system 602 in support of the various user input and output devices discussed above. Separately or in conjunction with each other and other hardware and software elements, the user interface software and user interface devices may support a graphical user interface, a natural user interface, or any other type of user interface, in which a user interface to a productivity application may be presented.

Communication between computing system 601 and other computing systems (not shown), may occur over a communication network or networks and in accordance with various communication protocols, combinations of protocols, or variations thereof. Examples include intranets, internets, the Internet, local area networks, wide area networks, wireless networks, wired networks, virtual networks, software defined networks, data center buses, computing backplanes, or any other type of network, combination of network, or variation thereof. The aforementioned communication networks and protocols are well known and need not be discussed at length here. In any of the aforementioned examples in which data, content, or any other type of information is exchanged, the exchange of information may occur in accordance with any of a variety of well-known data transfer protocols.

The functional block diagrams, operational scenarios and sequences, and flow diagrams provided in the Figures are representative of exemplary systems, environments, and methodologies for performing novel aspects of the disclosure. While, for purposes of simplicity of explanation, methods included herein may be in the form of a functional diagram, operational scenario or sequence, or flow diagram, and may be described as a series of acts, it is to be understood and appreciated that the methods are not limited by the order of acts, as some acts may, in accordance therewith, occur in a different order and/or concurrently with other acts from that shown and described herein. For example, those skilled in the art will understand and appreciate that a method could alternatively be represented as a series of interrelated states or events, such as in a state diagram. Moreover, not all acts illustrated in a methodology may be required for a novel implementation.

The descriptions and figures included herein depict specific implementations to teach those skilled in the art how to make and use the best option. For the purpose of teaching inventive principles, some conventional aspects have been simplified or omitted. Those skilled in the art will appreciate variations from these implementations that fall within the scope of the invention. Those skilled in the art will also appreciate that the features described above can be combined in various ways to form multiple implementations. As a result, the invention is not limited to the specific implementations described above, but only by the claims and their equivalents.

What is claimed is:

1. A computer-implemented method for dynamically monitoring sensor channels associated with a mobile communication device to detect a pre-determined health-related condition, the method comprising:
   selecting an initial group of sensor channels from sensor channels associated with the mobile communication device that are available for monitoring based on contextual sensor grouping information,
      wherein the contextual sensor grouping information identifies contextual groups of sensors that provide overlapping outputs that are interchangeable for detecting the pre-determined health-related condition;
   activating the initial group of sensor channels as active sensor channels;
   feeding outputs of the active sensor channels to a predictive model associated with the pre-determined health-related condition to infer at least one current health-state of a user of the mobile communication device;
   dynamically re-selecting, including deactivating, activating, or both, from the available sensor channels associated with the mobile communication device, the active sensor channels in an iterative or recursive manner based on the at least one current health-state of the user to minimize output overlap; and
   monitoring the active sensor channels to detect if the user has the particular predetermined physical or emotional health-related condition.

2. The computer-implemented method of claim 1, wherein dynamically re-selecting the active sensor channels comprises:
   responsive to a change in the at least one current health-state of the user, predicting sensor channels having outputs with decreased relevance for detecting the pre-determined health-related condition; and
   deactivating the sensor channels having outputs with decreased relevance.

3. The computer-implemented method of claim 1, wherein dynamically re-selecting the active sensor channels comprises:
   responsive to a change in the at least one current health-state of the user, predicting sensor channels having outputs with increased relevance for detecting the pre-determined health-related condition; and
   activating the sensor channels having outputs with increased relevance while using the contextual groups to minimize the output overlap of the active sensor channels.

4. The computer-implemented method of claim 1, wherein dynamically re-selecting the active sensor channels comprises:
   identifying status information associated with the mobile communication device,
   wherein the active sensor channels are re-selected based on the status information associated with the mobile communication device.

5. The computer-implemented method of claim 4, wherein the status information associated with the mobile communication device comprises information relating to power consumption of one or more sensor channels or battery status information associated with the mobile communication device.

6. The computer-implemented method of claim 4, wherein to select the initial group of sensor channels from the available sensor channels comprises:
   identifying sensor channels that provide overlapping outputs from the available sensor channels; and
   selecting sensor channels for the initial group of sensor channels having outputs that do not overlap.

7. The computer-implemented method of claim 1, further comprising:
   refining the predictive model based on the outputs of the active sensor channels.

8. The computer-implemented method of claim 1, further comprising:
   identifying the available sensor channels associated with the mobile communication device,
      wherein identifying the available sensor channels includes processing device attribute information or device status information associated with the mobile communication device, and
      wherein the available sensor channels associated with the mobile communication device are identified based on the device attribute information or the device status information associated with the mobile.

9. The computer-implemented method of claim 1, wherein the sensor grouping data structure identifies groups of sensor channels that provide overlapping outputs for use in detecting each of multiple different physical or emotional health-related conditions in a layered or hierarchical format.

10. The computer-implemented method of claim 1, further comprising:
    dynamically adjusting a sampling rate of one or more of the active sensor channels in an iterative or recursive manner based on one or more of the at least one current health-state of the user or status information associated with the mobile communication device.

11. An apparatus comprising:
    one or more computer readable storage media; and
    program instructions stored on the one or more computer readable storage media that, when executed by one or more processing systems, direct the processing systems to at least:
       select an initial group of sensor channels from sensor channels associated with a mobile communication device that are available for monitoring based on contextual sensor grouping information,
          wherein the contextual sensor grouping information identifies groups of sensors that provide overlapping outputs that are interchangeable for detecting a pre-determined health-related condition;
       activate the initial group of sensor channels as active sensor channels;
       feed outputs of the active sensor channels to a predictive model associated with the pre-determined health-related condition to infer at least one current health-state of a user of the mobile communication device; and based on the at least one current health-state of the user, dynamically re-select, including deactivating, activating, or both, from the available sensor channels associated with the mobile communication device, the active sensor channels in an iterative or recursive manner to minimize output overlap.

12. The apparatus of claim 11, wherein the instructions, when executed by the one or more processing systems, further direct the one or more processing systems to:
monitor the active sensor channels to detect if the user has the particular predetermined physical or emotional health-related condition.

13. The apparatus of claim 11, wherein to dynamically re-select the active sensor channels, the instructions, when executed by the one or more processing systems, further direct the one or more processing systems to:
responsive to a change in the at least one current health-state of the user,
predicting sensor channels having outputs with decreased relevance for detecting the pre-determined health-related condition;
predicting sensor channels having outputs with increased relevance for detecting the pre-determined health-related condition;
deactivating the sensor channels having outputs with decreased relevance; and
activating the sensor channels having outputs with increased relevance while using the contextual groups to minimize the output overlap of the active sensor channels.

14. The apparatus of claim 11, wherein to dynamically re-select the active sensor channels, the instructions, when executed by the one or more processing systems, further direct the one or more processing systems to:
identify status information associated with the mobile communication device,
wherein the active sensor channels are re-selected based on the status information associated with the mobile communication device.

15. The apparatus of claim 14, wherein the status information associated with the mobile communication device comprises information relating to power consumption of one or more sensor channels or battery status information associated with the mobile communication device.

16. The apparatus of claim 14, wherein to select the initial group of sensor channels from the available sensor channels, the instructions, when executed by the one or more processing systems, further direct the one or more processing systems to:
identify sensor channels that provide overlapping outputs from the available sensor channels; and
select sensor channels for the initial group of sensor channels having outputs that do not overlap.

17. The apparatus of claim 11, wherein the instructions, when executed by the one or more processing systems, further direct the one or more processing systems to:
refine the predictive model based on the outputs of the active sensor channels.

18. A health monitoring service comprising:
means for selecting an initial group of sensor channels from sensor channels associated with the mobile communication device that are available for monitoring based on contextual sensor grouping information,
wherein the contextual sensor grouping information identifies groups of sensors that provide overlapping outputs that are interchangeable for detecting the pre-determined health-related condition;
means for activating the initial group of sensor channels as active sensor channels;
means for feeding outputs of the active sensor channels to a predictive model associated with the pre-determined health-related condition to infer at least one current health-state of a user of the mobile communication device; and
means for dynamically re-selecting, including deactivating, activating, or both, from the available sensor channels associated with the mobile communication device, the active sensor channels in an iterative or recursive manner based on the at least one current health-state of the user to minimize output overlap.

19. The health monitoring service of claim 18, further comprising:
means for monitoring the active sensor channels to detect if the user has the particular predetermined physical or emotional health-related condition.

20. The health monitoring service of claim 18, wherein the means for dynamically re-selecting the active sensor channels comprises:
responsive to a change in the at least one current health-state of the user,
means for predicting sensor channels having outputs with increased or decreased relevance for detecting the pre-determined health-related condition;
means for deactivating the sensor channels having outputs with decreased relevance; and
means for activating the sensor channels having outputs with increased relevance while using the contextual groups to minimize the output overlap of the active sensor channels.

* * * * *